United States Patent
Lee et al.

(10) Patent No.: US 8,235,727 B2
(45) Date of Patent: Aug. 7, 2012

(54) DENTAL ARTICULATOR WITH ENDODONTIC MODULE

(75) Inventors: Charles Q. Lee, Lenexa, KS (US);
Jeffrey T. Scott, Shawnee, KS (US);
Amy H. Lee, Lenexa, KS (US)

(73) Assignee: Acadental, Inc., Mission, KS (US)

( * ) Notice: Subject to any disclaimer, the term of this patent is extended or adjusted under 35 U.S.C. 154(b) by 865 days.

(21) Appl. No.: 12/286,343

(22) Filed: Sep. 30, 2008

(65) Prior Publication Data

US 2009/0123898 A1    May 14, 2009

Related U.S. Application Data

(63) Continuation-in-part of application No. 11/784,806, filed on Apr. 10, 2007.

(51) Int. Cl.
*G09B 23/28*    (2006.01)

(52) U.S. Cl. .......................................... 434/263

(58) Field of Classification Search .................. 434/263, 434/264; 433/54, 57, 58, 59, 61, 62, 63, 433/64, 68
See application file for complete search history.

(56) References Cited

U.S. PATENT DOCUMENTS

| | | | | |
|---|---|---|---|---|
| 1,205,437 A * | 11/1916 | Delabarre | .................... | 434/264 |
| 2,103,058 A * | 12/1937 | Burtenshaw | .................. | 434/264 |
| 3,570,127 A * | 3/1971 | Getz | ................................ | 433/55 |
| 3,931,679 A * | 1/1976 | Carter | ........................... | 434/264 |
| 3,965,576 A * | 6/1976 | Eveland | ......................... | 433/56 |
| 4,067,109 A * | 1/1978 | Engeser | ........................ | 434/264 |
| 4,163,319 A * | 8/1979 | Ouaknine | ....................... | 433/60 |
| 4,792,306 A * | 12/1988 | Duplantis | .................... | 434/264 |
| 4,968,256 A * | 11/1990 | Lang et al. | .................... | 434/263 |
| 5,073,109 A * | 12/1991 | El Hadary | ....................... | 433/57 |
| 5,098,289 A * | 3/1992 | Feher | ............................... | 433/57 |
| 5,108,292 A * | 4/1992 | Kirk et al. | ..................... | 434/263 |
| 5,320,528 A * | 6/1994 | Alpern et al. | ................... | 433/58 |
| 5,605,456 A * | 2/1997 | Young | ............................. | 433/60 |
| 5,645,425 A * | 7/1997 | Callne | ........................... | 433/54 |
| 5,766,007 A * | 6/1998 | Huffman | ......................... | 433/61 |
| 6,450,809 B1 * | 9/2002 | Iverson | .......................... | 433/64 |
| 6,520,775 B2 | 2/2003 | Lee | | |
| 6,988,894 B2 | 1/2006 | Lee | | |
| 7,544,061 B2 * | 6/2009 | Poitras | ......................... | 434/263 |
| 2008/0220404 A1 * | 9/2008 | Woidschutzke | .............. | 434/263 |

* cited by examiner

*Primary Examiner* — Kurt Fernstrom
(74) *Attorney, Agent, or Firm* — D. A. N. Chase; Erickson, Kernell, Derusseau & Kleypas, LLC

(57) ABSTRACT

A dental articulator for use in dental education simulates the human mouth and has an adjustable hinge that interconnects upper and lower carrier trays for movement to and from a closed position. Modules of imitation gums and teeth are secured in the carrier trays by neodymium magnets. The hinge structure in the articulator is selectively movable to shift the jaw axis to a position to provide the desired alignment of the upper and lower teeth when the jaw is closed or demonstrate a misaligned condition. A dental training module may be installed which, upon removal from the articulator, has a pair of separable sections encasing a tooth to permit release of the tooth and removal from the module so that a completed treatment may be evaluated.

13 Claims, 4 Drawing Sheets

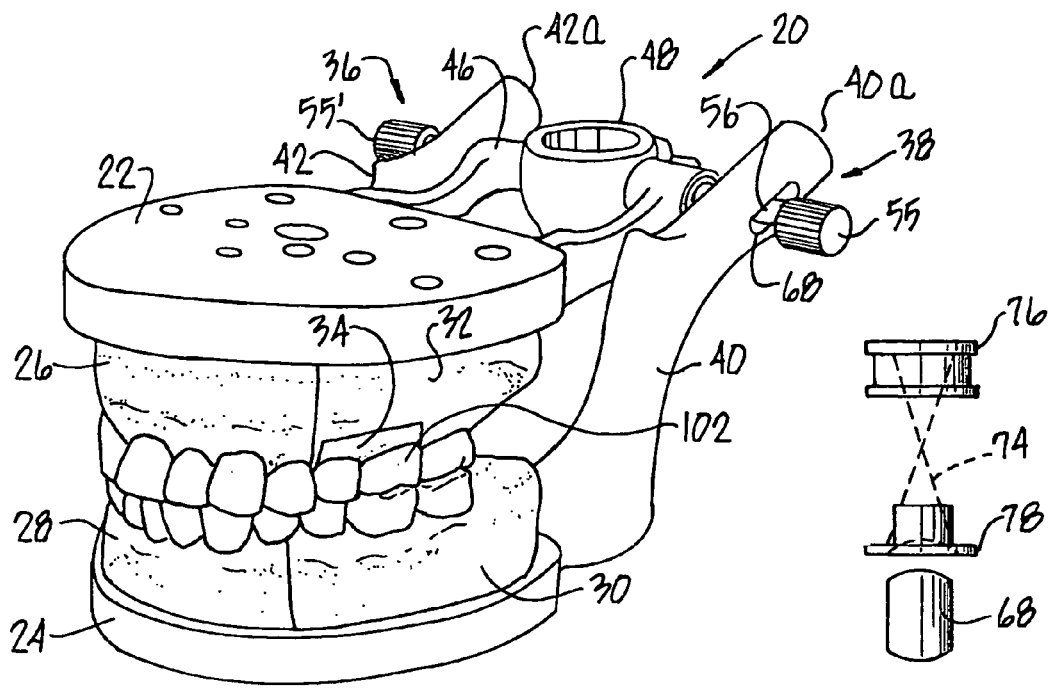
Fig. 1
Fig. 5
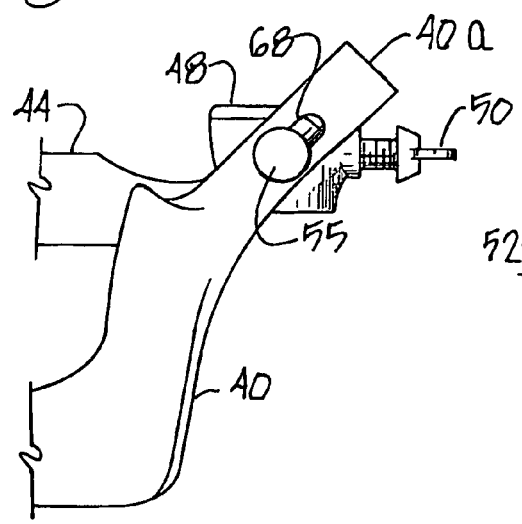
Fig. 2
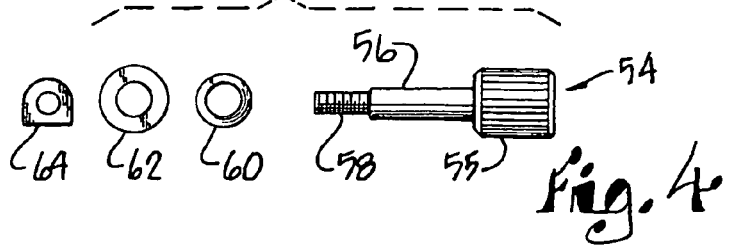
Fig. 3
Fig. 4

DENTAL ARTICULATOR WITH ENDODONTIC MODULE

This application is a continuation-in-part of application Ser. No. 11/784,806, filed Apr. 10, 2007.

FIELD OF THE INVENTION

This invention relates to improvements in dental articulators and simulated components of the human mouth utilized as a teaching tool and a demonstrative aid, and to the training of dentists or dental students in dental procedures.

BACKGROUND OF THE INVENTION

As a training aid in dentistry, a replica of the mouth or manikin is utilized so that the student can learn and practice dental procedures and develop a high level of skill before performing a procedure on a patient. The complexity of such procedures and the high level of precision required is set forth, for example, in U.S. Pat. No. 6,988,894, owned by the assignee herein. The manikin or dental articulator is a replica of the human mouth containing gum and tooth modules that may be inserted and removed as needed for a particular procedure. Also, an articulator may be used to show a patient a particular dental condition or facilitate explanation of a particular procedure and the manner in which it is performed.

Dental articulators, however, are typically provided with a fixed jaw axis which does not facilitate adjustment of the relative positions of the upper and lower jaws to correct misalignment that may occur in the day-to-day use of the articulator. Furthermore, there are instances in which it is desired to demonstrate an intentional misalignment by shifting the jaw axis, or correcting a misaligned manikin by adjusting the axis to a proper location. Gum and tooth modules may not be readily removed from the articulator, and procedures performed on embedded natural or artificial teeth may not be easily evaluated.

SUMMARY OF THE INVENTION

In an embodiment of the present invention an improved dental articulator is provided for use in dental education. The articulator simulates the human mouth and provides an adjustable hinge which permits proper alignment and, therefore, proper occlusion to be maintained, or an intentional misalignment demonstrated, for use in training in dental school and by dentists to demonstrate to patients.

One aspect of the present invention is the utilization of hinge structure that provides a jaw axis in a dental articulator that is selectively movable transversely to a fixed position where the axis provides the desired alignment of the upper and lower teeth when the jaw is closed. Alignment is further assured in an embodiment of the present invention by the utilization of an adjustable ball and recess connection to the upper jaw which provides both a proper lateral and vertical orientation with respect to the lower jaw.

Another aspect of the invention is the utilization of a hinge structure in a dental articulator having components that are selectively movable to a fixed position where the jaw axis provides the desired alignment in the closed position of the upper and lower teeth.

A further aspect of the invention is to provide hinge pins in a dental articulator that establish the desired jaw axis and are selectively movable to positions that provide proper alignment of the upper and lower jaws, and which may be secured in such positions to maintain the aligned condition. Furthermore, each hinge pin is held by a spring and, when desired, may be moved against the bias of the spring to shift the jaw axis to a misaligned condition for demonstration purposes and then released for return to the aligned condition.

Additionally, the present invention in another aspect thereof provides an endodontic training module adapted to be removably installed in a manikin and which includes an insert having a endodontic tooth therein upon which a student may perform a procedure while the module is in the manikin. The insert has a pair of separable sections encasing the tooth while the insert is in the module, and permitting release of the tooth upon removal of the insert from the module after an endodontic procedure so that the completed treatment may be evaluated.

An additional aspect of the invention is the provision of a carrier tray for a dental articulator having a base plate recessed at desired module locations and provided with a series of flat, side-by-side permanent magnets in each of the recesses presenting surfaces at each of the module locations substantially flush with the mounting surface, each of the modules having a plate of magnetic material therein overlying the magnets at the corresponding location to thereby releasably hold the modules in the tray.

Other advantages of this invention will become apparent from the following description taken in connection with the accompanying drawings, wherein is set forth by way of illustration and example, an embodiment of the present invention.

BRIEF DESCRIPTION OF THE DRAWINGS

FIG. 1 is a side perspective view of the dental articulator with the mouth closed.

FIG. 2 is a fragmentary view of the articulator showing two of the members that are connected to the upper and lower carriers, as seen looking along the axis of the hinge.

FIG. 3 is a detail view of one of the axle hinge components partially broken away and shown in cross section, a compression spring being illustrated in broken lines.

FIG. 4 is an exploded view of the hinge parts.

FIG. 5 is a detail view of the compression spring and shoulder ring.

DETAILED DESCRIPTION

FIGS. 1-14

Figure 6:
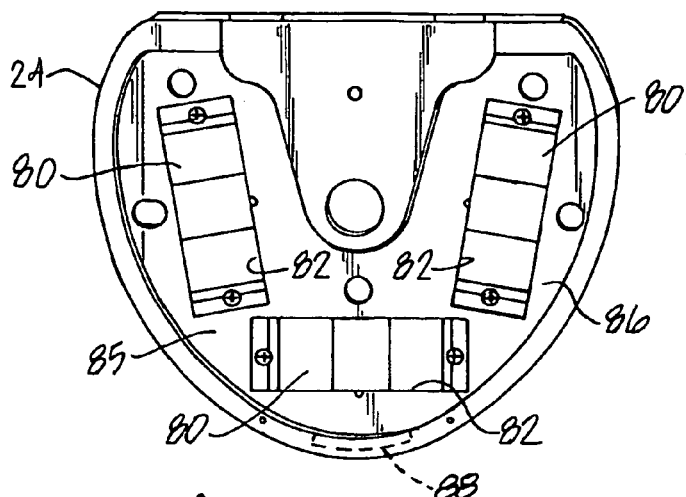
FIG. 6 is a plan view of the lower carrier tray.

Referring initially to FIGS. 1 and 2, a dental articulator 20 presents a manikin having an upper carrier tray 22 and a lower carrier tray 24 which receive and hold individual modules of imitation gums and teeth, upper such module 26 and two lower modules 28 and 30 being seen in FIG. 1. Also, as will be discussed more fully hereinafter, the upper tray 22 receives and holds an endodontic module 32 having a breakaway insert 34. The trays 22 and 24 are rotatable about a transverse axis provided by adjustable, left and right hinge components 36 and 38 which establish an axis about which articulated members connected to the trays 22 and 24 rotate; specifically, axially spaced outer, lower members 40 and 42 connected to the rear edge of lower carrier tray 24 in the conventional manner, and spaced inner, upper members 44 and 46 connected to the rear edge of the upper carrier tray 22. To open and close the articulator (shown in the closed condition), one or both of the carrier trays 22 and 24 are rotated about the axis provided by the hinge components 36 and 38. A mounting ring 48 is integral with inner members 44 and 46 and centered therebetween to provide a means of supporting the manikin on a post (not shown) and tightening ring 48 thereon by a manually adjustable screw 50, as is conventional.

The hinge structure is shown more fully in FIGS. 3-5 where the hinge component 38 and associated parts are revealed in detail, it being understood that hinge component 36 on the opposite side of ring 48 is constructed in the same manner to provide a continuous axis 52 from outer member 40 to outer member 42. A hinge component or pin 54 has an enlarged end presenting a knob 55 coaxial with the shaft 56 of the pin 54, the pin 54 terminating at its opposite end in a threaded portion 58 of smaller diameter. As will be discussed, the hinge pin assembly is completed by a shoulder ring 60, washer 62 and nut 64.

Outer member 40 has a tubular upper end portion 40a through which shaft 56 extends at a right angle. FIG. 3 shows the hinge pin 54 in place with shaft 56 extending through an elongated opening 68 near the upper end of outer member 40, across end portion 40a and inward into an axial opening 70 in the outer end of inner member 44 aligned with axis 52. The hinge is assembled by inserting shaft 56 with shoulder ring 60 thereon through opening 68 and on into axial opening 70 with washer 62 disposed between members 40 and 44. An opening 72 in the member 44 communicates with axial opening 70 to permit insertion of nut 64 in the assembly of the hinge. It should be noted that the axial opening 70 in the outer end portion of inner member 44 is oversized with respect to the diameter of the shaft 56 of the hinge pin 54 to permit adjustment of the axis 52 as will be discussed.

Referring to FIGS. 3 and 5, a compression spring in the hollow outer end of member 40 operates between a removable end plug 76 and a cut 78 that mates with shoulder ring 60 on the shaft 56 of hinge pin 54. The spring 74, therefore, maintains shaft 56 at the bottom end of elongated opening 68 as seen in FIGS. 2 and 3.

The adjustable hinge component 36 associated with tubular end portion 42a of member 42 is constructed in the same manner as described above for hinge component 38 and completes the axis 52 about which the upper carrier tray 22 may be rotated to simulate the opening and closing of the jaw. As will be discussed more fully hereinbelow, adjustment of the axis 52 is provided by the oversize opening 70 and cooperating parts in each of the two hinge assemblies.

Figure 7:
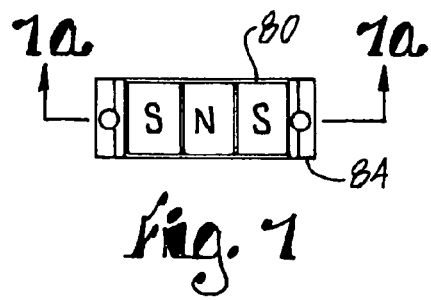
FIG. 7 is a detail view showing one of the magnet assemblies utilized in the tray of FIG. 6.
Figure 7A:
FIG. 7a is a longitudinal cross-sectional view of the magnet assembly of FIG. 7.
Figure 8:
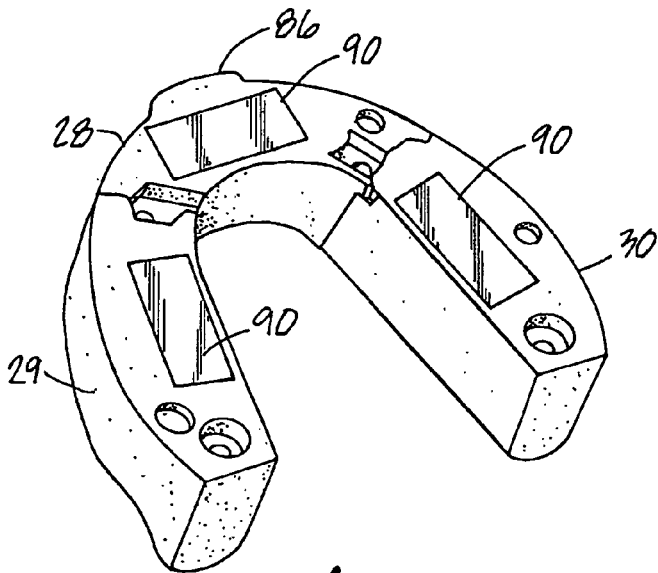
FIG. 8 is a perspective view looking at the interior face of modules that are magnetically held within the lower carrier tray.
Figure 9:
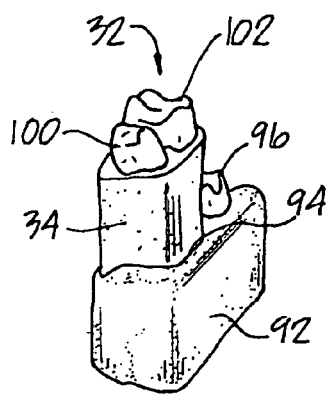
FIG. 9 is a perspective view of the endodontic module removed from the carrier tray, a breakaway insert containing a simulated tooth being shown partially withdrawn from the module.

Referring to FIGS. 6-8, the lower carrier tray 24 is shown in detail. In FIG. 6 the modules 28 and 30 are removed and, additionally, a module 29 (FIG. 8) not visible in FIG. 1. The tray 24 is composed of a nonmagnetic material such as aluminum and has three magnetic assemblies 80 therein, each of which is secured in a corresponding rectangular recess 82 and creates a closed magnetic field. Each of the magnet assemblies 80 comprises three neodymium magnets side-by-side presenting upwardly facing, alternating poles as shown in FIG. 7 (south, north and south). Each of the three magnet assemblies 80 is held in a non-magnetic, e.g. plastic, frame 84 as seen in FIGS. 7 and 7a. Preferably, the total thickness of the magnet and frame assembly is approximately three millimeters with the magnets themselves having a thickness of less than two millimeters, and thus the assembly is accommodated without increasing the thickness of the tray. The rectangular recesses 80 in tray 24 are complimental to the frame 84 and provide a flush fit with the upper surfaces of the magnets 80 co-planar with the interior surface 85 of the tray 24. Upper tray 22 is of identical construction.

FIG. 8 shows the two gum modules 28 and 30 (teeth are not shown) seen in FIG. 1 and a module 29 hidden from view in FIG. 1 which, as a group, are insertable into lower tray 24, a tab 86 at the anterior tip thereof being received in a corresponding slot 88 in the tray 24. Each of the modules 28, 29 and 30 has a rectangular plate 90 of magnetic material (such as steel) embedded therein with its outer surface flush with the bottom surface of each of the modules. These plates 90 register with corresponding magnet assemblies 80 upon insertion of the modules into the tray, thereby securing the modules within the tray until forceably released therefrom by a quick manual pull on the module. Though illustrated herein in the lower tray 24, it is to be understood that the magnetic assemblies 80 may also be used to secure modules in the upper tray 22 of the articulator 20.

Use of the articulator of the present invention in connection with an endodontic procedure is illustrated in FIGS. 9-14. The module 32 comprises a simulated plastic gum 92, a preformed socket 94 in the module, a dummy tooth 96, and the breakaway insert 34 (partially withdrawn) having a dummy tooth 100 and a simulated tooth 102 (either upper or lower) upon which an endodontic procedure may be practiced.

Figure 10:
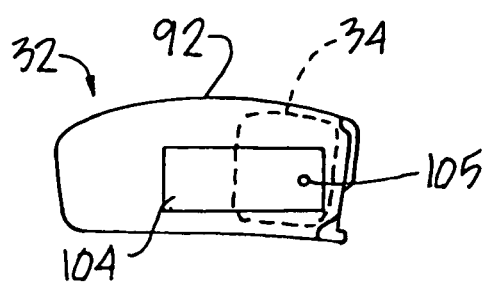
FIG. 10 is a bottom view of the endodontic module.
Figure 11:
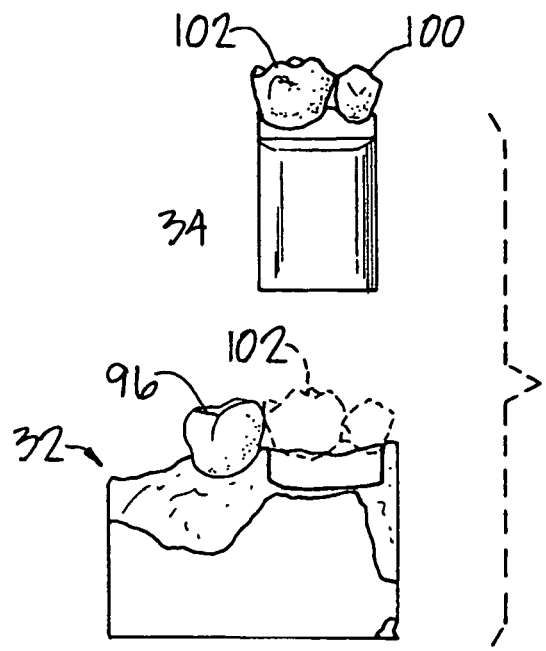
FIG. 11 is an exploded, elevational view showing the insert fully withdrawn from the module, the phantom lines illustrating the teeth of the insert when the latter is fully installed in the endodontic module before removal therefrom.

FIG. 10 shows the bottom of the module 32 where a plate of magnetic material 104 is recessed into the base of the module for releasably securing the module in the upper carrier tray 22 of the articulator (FIG. 1). After a dental procedure is performed on the tooth 102 (which may be a lower tooth as well as an upper tooth procedure), the module 32 is released from the manikin so that the tooth 102 may be inspected and the quality of the student's work determined. The insert 34 is withdrawn as illustrated in FIG. 11, facilitated by a release hole 105 in the base of the module 32. A slot 106 in the base of the insert 34 (FIG. 12) permits the breakaway action by insertion of a small coin or similar object (not shown) into the slot 106 and, by a twisting action, separating the insert into its two mating sections 34a and 34b. FIGS. 13 and 14 reveal a small tab 108 on section 34b which is tightly received within an opening 110 in section 34a to hold the mating sections together in properly aligned relationship until separation.

Figure 12:
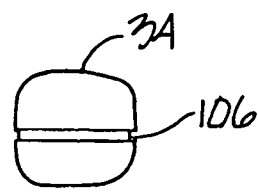
FIG. 12 is a bottom view of the insert.
Figure 13:
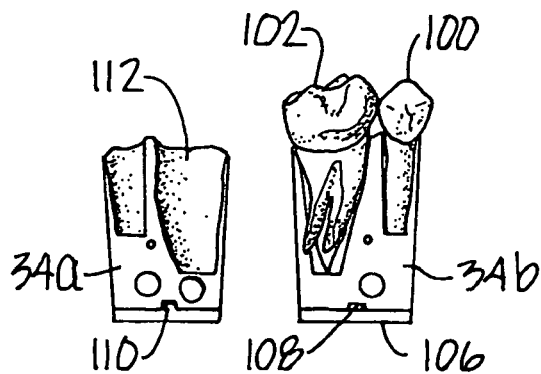
FIG. 13 is an exploded, elevational view showing the two sections of the insert after they are separated, both sections shown from the interior side.
Figure 14:
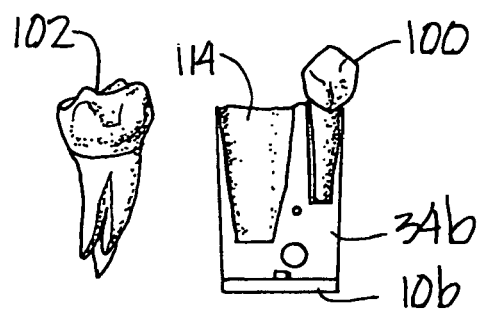
FIG. 14 is an exploded view in elevation showing the simulated tooth removed from the insert.

As may be appreciated from FIGS. 13 and 14, the simulated tooth 102 is received within aligned recesses 112 in section 34a and 114 in section 34b when the insert 34 is in its closed condition as seen in FIGS. 11 and 12. Accordingly, when the sections 34a and 34b are released, the endodontic tooth 102 previously held in the recesses 112, 114 may be removed as illustrated in FIG. 14 and the work of the student evaluated by the instructor. For example, for a root canal procedure, the instructor can visualize complete treatment of the canals as well as check for perforations that may have been made through the canal or pulp floor during the procedure. This is accomplished by simple visual inspection without the necessity of radiographic analysis, for example, that would be required in order to evaluate an encased tooth. Furthermore, the endodontic module 32 may be reused repeatedly by replacing the insert 34.

FIGS. 15-18

Figures 15, 16:
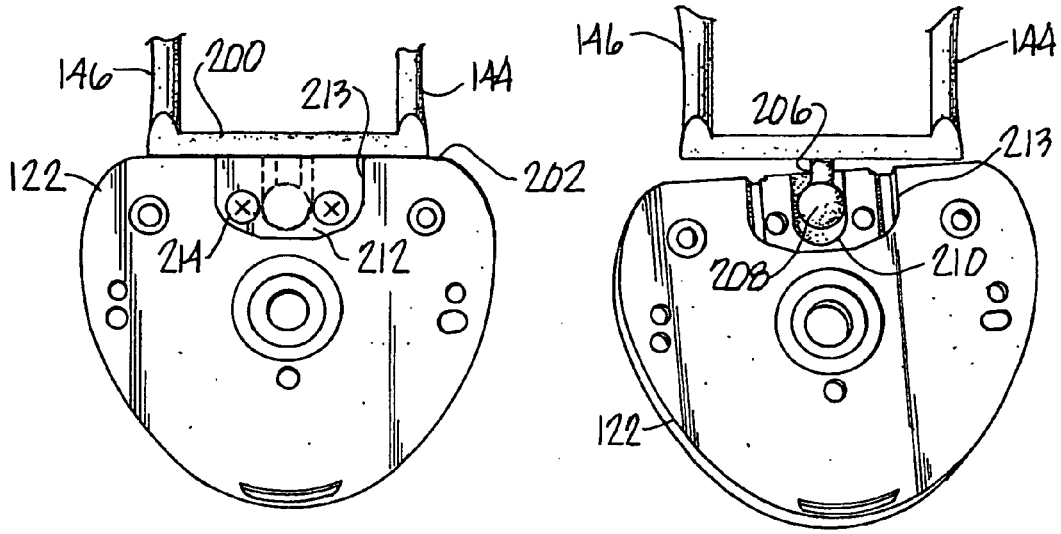
FIG. 15 is a fragmentary, plan view showing a modified form of upper carrier tray which provides a ball and recess connection to the upper support members.
FIG. 16 is a view similar to FIG. 15 illustrating a maximum lateral displacement of the adjustable tray, parts being broken away to reveal the ball and recess connection.
Figure 18:
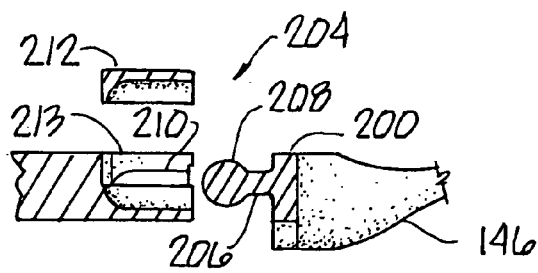
FIG. 18 is an exploded, detail view showing the components of the ball and recess connection.
Figure 17:
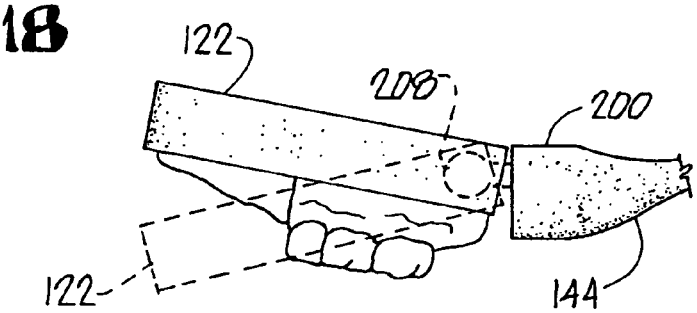
FIG. 17 is a side elevational view of the carrier tray of FIGS. 15 and 16 illustrating the ability of the connection to provide up and down adjustability.

A modified form of carrier tray 122 is shown in FIGS. 15-18 and provides additional adjustability to assure proper alignment in the closed condition of the articulator 20. Spaced upper arm members 144 and 146 are interconnected at their distal ends by a crossbar 200 shown in FIG. 15 engaging the rear edge 202 of tray 122. This is the normal position of the crossbar 200 when the adjustable, left and right hinge components 36 and 38 described hereinabove provide adequate adjustability to properly align the upper and lower carrier trays 22 and 24 as shown in FIG. 1. However, if additional adjustment is required to provide the proper alignment, the upper carrier tray 122 may be shifted to the left or right as illustrated in FIG. 16 or pivoted upwardly or downwardly as illustrated in FIG. 17, by a ball and recess connection shown in detail in the exploded view of FIG. 18.

More particularly, the crossbar 200 has a shank or stem 206 at its longitudinal center projecting forwardly and presenting a ball 208 which is received within a corresponding recess 210 in the rear edge 202 of tray 122 to provide a ball-and-socket connection (FIGS. 15, 16 and 17). The ball 208 is held in socket 210 by a cover plate 212 received in an opening 213 and secured by a pair of screws 214. The plate 212 is removed in FIG. 16 to reveal the shank 206 and ball 208, and is shown in place in opening 213 in FIG. 15 secured by screws 214 to thereby clamp the ball 208 and lock it in the selected position. In FIG. 15 the ball 208 is essentially fully inserted in the slot 210 and the bar 200 is in engagement with surface 202, whereas in FIG. 16 an extreme adjustment is illustrated and shows rotation of the tray 122 to the right. Accordingly, left to right adjustability is provided by the ball and recess connection upon loosening the screws 214, shifting the tray 122 to the desired position that will provide proper alignment of the teeth, and then tightening the screws 214.

Furthermore, up and down adjustability about the ball 208 is also provided by the ball-and-socket connection upon loosening the screws 214 and swinging the tray 122 to the desired position. Comparison of the full and broken lines in FIG. 17 illustrates the capability of providing a range of adjustability that assures accurate positioning of the simulated upper teeth relative to the lower teeth at the proper alignment or demonstration of an intentional misalignment. Also, it should be appreciated that the lower carrier tray 24 (FIGS. 1 and 6) may be modified in the same manner as described above for upper carrier tray 122, thereby providing either or both trays with full adjustability.

It is to be understood that while certain forms of embodiments of this invention have been illustrated and described, it is not limited thereto, except insofar as such limitations are included in the following claims and allowable equivalents thereof.

Having thus described the invention, what is claimed as new and desired to be secured by Letters Patent is:

1. A dental articulator comprising:
an upper carrier tray supporting simulated upper gums and upper teeth,
a lower carrier tray supporting simulated lower gums and lower teeth, and
a pair of articulated members connected with said upper and lower trays respectively for movement of one of said trays about an axis to and from a closed position in which said upper and lower teeth are in contact to simulate a closed mouth in which said teeth are in a desired alignment, and
hinge structure interconnecting said members and presenting said axis, and including an adjustable hinge component selectively movable transversely with respect to said axis to a fixed position where said axis provides said desired alignment in the closed position of said upper and lower teeth,
said members having aligned openings therein receiving said hinge component for said transverse movement thereof to said fixed position to provide the desired alignment in the closed position of said upper and lower teeth.

2. The dental articulator as claimed in claim 1, wherein said articulated members include a second pair thereof connected with respective upper and lower carrier trays, said members of said second pair having aligned openings therein receiving a second hinge component selectively movable transversely with respect to said axis to a second fixed position where said axis provides the desired alignment in the closed position of said upper and lower teeth.

3. The dental articulator as claimed in claim 2, wherein each of said pairs of articulated members includes an inner member connected with one of said trays and an outer member connected with the other of said trays, each of said hinge components comprising a hinge pin of predetermined diameter, the opening in each of said inner members being larger than the diameter of the associated hinge pin to permit movement of said hinge pins to said fixed positions to provide the desired alignment, and structure on said hinge pins and said inner members for releasably securing the hinge pins in said fixed positions.

4. The dental articulator as claimed in claim 3, wherein the opening in each of said outer members is elongated in a direction transversely of said axis, and wherein each of said outer members has an elongated, resilient element in the opening thereof engaging the respective hinge pin to permit movement of said trays against the bias of said elements to positions demonstrating a misaligned condition of said teeth.

5. The dental articulator as claimed in claim 1, wherein said hinge component comprises a hinge pin of a predetermined diameter, said aligned openings being larger than said diameter to permit movement of said trays to positions demonstrating a misaligned condition of said teeth.

6. The dental articulator as claimed in claim 5, wherein one of said members is provided with a resilient element engaging said hinge pin to permit relative movement of said trays against the bias of said element away from a normal position to said misaligned condition.

7. A dental articulator comprising:
an upper carrier tray supporting simulated upper gums and upper teeth, a lower carrier tray supporting simulated lower gums and lower teeth, articulated members connected with said upper and lower trays for movement of one of said trays about an axis to and from a closed position in which said upper and lower teeth are in contact to simulate a closed mouth in which said teeth are in a desired alignment, hinge structure interconnecting said members and presenting said axis, and including a hinge component selectively movable transversely with respect to said axis to a fixed position where said axis provides said desired alignment in the closed position of said upper and lower teeth, one of said carrier trays having a baseplate providing a mounting surface for modules containing artificial teeth, said surface having a permanent magnet therein at a module location, and a dental training module removably installed at said location and held by said magnet, said module having artificial gum structure including a breakaway insert with a pair of separable sections presenting a sleeve encasing a tooth while the insert is in the module whereby, upon removal of the insert from the module after a dental procedure, the tooth may be released from the insert to permit evaluation of the completed treatment.

8. A dental articulator comprising:

an upper carrier tray supporting simulated upper gums and upper teeth, a lower carrier tray supporting simulated lower gums and lower teeth, structure providing a jaw axis and having an arm connected with one of said trays for movement thereof about said axis to and from a closed position in which said upper and lower teeth are in contact to simulate a closed mouth in which said teeth are in a desired alignment, said one tray having a rear portion provided with a recess therein, a connector on said arm projecting therefrom and presenting a ball received within said recess to permit adjustment of said one tray to a position at which said upper and lower teeth are in said desired alignment, and a clamping element on said rear portion for securing said ball within said recess to hold said upper and lower teeth in said desired alignment.

9. The dental articulator as claimed in claim 8, wherein said arm includes spaced members and a normally horizontally extending bar spanning said members, said connector being rigidly secured to said bar.

10. The dental articulator as claimed in claim 9, wherein said connector has a shank terminating in said ball at a distal end thereof.

11. The dental articulator as claimed in claim 9, further comprising a clamping element on said rear portion for securing said ball within said recess to hold said upper and lower teeth in said desired alignment.

12. The dental articulator as claimed in claim 8, wherein said one tray is the upper tray.

13. A dental articulator comprising:

an upper carrier tray supporting simulated upper gums and upper teeth, a lower carrier tray supporting simulated lower gums and lower teeth, structure providing a jaw axis and having an arm connected with one of said trays for movement thereof about said axis to and from a closed position in which said upper and lower teeth are in contact to simulate a closed mouth in which said teeth are in a desired alignment, said one tray having a rear portion provided with a recess therein, a connector rigidly secured to said arm projecting therefrom and presenting a ball received within said recess to permit adjustment of said one tray to a position at which said upper and lower teeth are in said desired alignment, said arm including spaced members and a normally horizontally extending bar spanning said members, said connector being rigidly secured to said bar, and a clamping element on said rear portion for securing said ball within said recess to hold said upper and lower teeth in said desired alignment.

* * * * *